United States Patent
Ouyang et al.

(10) Patent No.: US 11,185,108 B2
(45) Date of Patent: Nov. 30, 2021

(54) ELECTRONIC CIGARETTE WITH ROTATABLE MOUTHPIECE

(71) Applicant: Shenzhen First Union Technology Co., Ltd., Shenzhen (CN)

(72) Inventors: Zhi Ouyang, Shenzhen (CN); Meng Li, Shenzhen (CN); Huiyun Chen, Shenzhen (CN); Zhongli Xu, Shenzhen (CN); Yonghai Li, Shenzhen (CN)

(73) Assignee: Shenzhen First Union Technology Co., Ltd., Guangdong (CN)

( * ) Notice: Subject to any disclaimer, the term of this patent is extended or adjusted under 35 U.S.C. 154(b) by 460 days.

(21) Appl. No.: 15/871,979

(22) Filed: Jan. 15, 2018

(65) Prior Publication Data
US 2018/0338526 A1    Nov. 29, 2018

(30) Foreign Application Priority Data
May 25, 2017 (CN) .......................... 201720590675.5

(51) Int. Cl.
| | |
|---|---|
| *A24F 40/40* | (2020.01) |
| *A24F 7/02* | (2006.01) |
| *A61M 15/06* | (2006.01) |
| *A61M 15/00* | (2006.01) |
| *H05B 3/44* | (2006.01) |

(52) U.S. Cl.
CPC ............... *A24F 7/02* (2013.01); *A24F 40/40* (2020.01); *A61M 15/0021* (2014.02); *A61M 15/06* (2013.01); *H05B 3/44* (2013.01); *A61M 2205/8206* (2013.01)

(58) Field of Classification Search
CPC ............................ A24F 7/02; A61M 15/0021
USPC ......................................................... 131/329
See application file for complete search history.

(56) References Cited

U.S. PATENT DOCUMENTS

| | | | |
|---|---|---|---|
| 8,314,591 B2* | 11/2012 | Terry .................. | A24F 47/008 320/114 |
| 8,430,271 B2* | 4/2013 | Poulard ................ | A61M 11/02 128/200.23 |
| 2013/0160780 A1* | 6/2013 | Matsumoto ............... | B65B 1/20 131/329 |
| 2015/0158288 A1* | 6/2015 | Gemelli ................ | B41F 17/006 101/333 |

(Continued)

FOREIGN PATENT DOCUMENTS

| | | |
|---|---|---|
| CN | 204273237 U | 4/2015 |
| CN | 205728058 U | 11/2016 |
| WO | 2016162446 A1 | 10/2016 |

*Primary Examiner* — Eric Yaary
*Assistant Examiner* — Russell E Sparks
(74) *Attorney, Agent, or Firm* — Proi Intellectual Property US; Klaus Michael Schmid

(57) ABSTRACT

The present disclosure discloses an electronic cigarette with a rotatable mouthpiece. The electronic cigarette comprises a battery assembly and an atomizing assembly. The battery assembly comprises a battery and a casing. The atomizing assembly comprises a mouthpiece, an outer sleeve, and a cartridge. The outer sleeve is hinged to casing through a cardinal axis. The cardinal axis is accommodated in a guide rail groove, and is slidable along the guide rail groove. The sliding direction of the cardinal axis is the same as the axial direction of the casing. After using the electronic cigarette, the mouthpiece could be rotated and stored in the casing conveniently, and keep cleaning.

10 Claims, 6 Drawing Sheets

(56) References Cited

U.S. PATENT DOCUMENTS

| | | |
|---|---|---|
| 2015/0297843 A1 | 10/2015 | Lu et al. |
| 2018/0084831 A1* | 3/2018 | Mironov .............. A61M 11/042 |
| 2018/0339118 A1* | 11/2018 | Ouyang .............. A61M 11/042 |
| 2019/0150505 A1* | 5/2019 | Ceppi ................... A61M 15/06 |

* cited by examiner

ELECTRONIC CIGARETTE WITH ROTATABLE MOUTHPIECE

CROSS REFERENCE TO RELATED APPLICATIONS

The present application claims priority to Chinese patent application CN 201720590675.5 filed on May 25, 2017.

TECHNICAL FIELD

The present disclosure relates to electronic cigarette field, especially to an electronic cigarette with a rotatable mouthpiece.

BACKGROUND

Smoke from burning tobacco contains dozens of carcinogen. For example, tars in the smoke have a big influence on the human health. And also the second hand smoke hurts human body a lot. At present, smoking is prohibited in most public places. To meet demands of smokers, the electronic cigarette is a better alternative.

At present, mouthpieces of the most electronic cigarettes are exposed in the air, and they are easily to be polluted by dust, oil or other pollutions. And it affects the user experiences. Only few electronic cigarettes would be accommodated in packages after using. Extra packages for accommodation will increase the cost and it is not convenient too.

For example, in Chinese patent file CN201620403775.8, it discloses "A mouthpiece and an electronic cigarette having the same". The mouthpiece is rotatably accommodated in an accommodation groove, so that it can be prevented from pollution. From FIG. 1, it can be known that although the mouthpiece is accommodated, a portion of the mouthpiece is still exposed in the air. And it cannot avoid the environment pollution totally. Another example, Chinese patent file CN201420654658.X discloses "A baking-type electronic cigarette with retractable mouthpiece". One end of a guide rail connects with the mouthpiece, and a groove is defined in the casing so that the guide rail could move up and down along the groove. In that disclosure, in non-using status, the mouthpiece will not protrude from the surface of the products too much. But it cannot avoid the total pollution of the mouthpiece too.

SUMMARY

The object of the present disclosure is to provide an electronic cigarette which could solve the technical problem in the prior art and store the mouthpiece totally. The electronic cigarette of the present disclosure has a low cost and could be operated easily.

To solve the above problem, the present disclosure provides an electronic cigarette with a rotatable mouthpiece. The electronic cigarette comprises a battery assembly and an atomizing assembly which connected with the battery assembly. The battery assembly comprises a battery and a casing. The atomizing assembly comprises a mouthpiece, a cartridge, and an outer sleeve. The outer sleeve is hinged to the casing through a cardinal axis.

In one embodiment of the present disclosure, the cardinal axis is accommodated in a guide rail groove. The cardinal axis is slidable along the guide rail groove. And the sliding direction of the cardinal axis is the same as an axial direction of the casing.

In another embodiment of the present disclosure, an upper portion of the casing of the battery assembly comprises a side ridge. The outer sleeve is hinged to the side ridge through the cardinal axis. And the guide rail groove is defined in the side ridge.

In another embodiment of the present disclosure, in using status, the cardinal axis is positioned at the upper or middle portion of guide rail groove. And an end portion of the outer sleeve is accommodated in the groove of the upper portion of the casing.

In another embodiment of the present disclosure, in accommodation status, the cardinal axis is positioned at the bottom of the guide rail groove. The mouthpiece is accommodated in a groove of an upper portion of the casing. And the outer surface of the outer sleeve laminates with an upper portion of the casing totally.

In another embodiment of the present disclosure, the mouthpiece of the atomizing assembly and the outer sleeve are a one-piece structure or a detachable structure.

In another embodiment of the present disclosure, the cartridge and outer sleeve are a detachable structure.

In another embodiment of the present disclosure, the outer sleeve has vertical slots defined in a side surface. The cartridge has a protruding portion formed on an outer surface. The position of the protruding portion is correspondent with the position of the slots. And the protruding portion protrudes from the outer surface of the outer sleeve.

In another embodiment of the present disclosure, a total number of the slots is two. And a total number of the protruding portions is two, correspondingly.

In another embodiment of the present disclosure, the outer sleeve has an end cap, and the end cap and the mouthpiece are placed on two sides of the outer sleeve respectively.

The advantages of the disclosure are that the side ridge has a guide rail groove. The atomizing assembly is slidable up and down along the guide rail groove. And the atomizing assembly could be rotated from 0 to 180 degrees. In the case that the atomizing assembly is rotated 0 degrees or 180 degrees, an outer surface of the outer sleeve laminates with the upper portion of the casing tightly. So the electronic cigarette could keep cleaning, and at the same time save space. Protect the user privacy.

DETAILED DESCRIPTION

Figure 1:
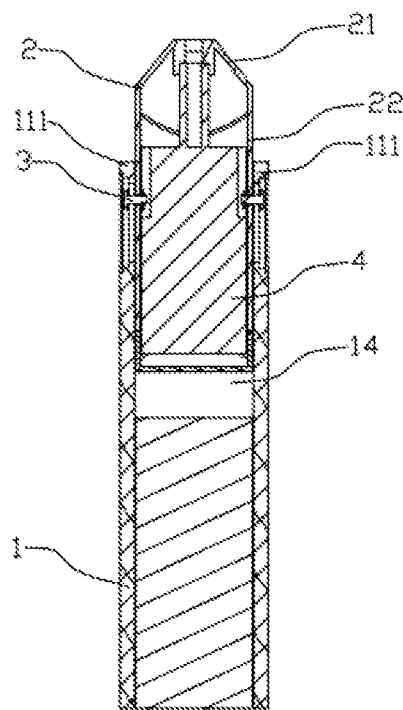
FIG. 1 is a cross-section of the electronic cigarette with a rotatable mouthpiece in using status.
Figure 2:
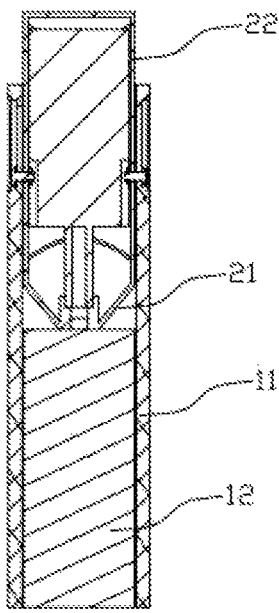
FIG. 2 is a cross-section of the electronic cigarette with a rotatable mouthpiece in accommodation status.

Referring the figures of the disclosure hereafter makes a further description of the electronic cigarette with a rotatable mouthpiece of the present disclosure.

FIGS. 1-8 show a first embodiment of the electronic cigarette with a rotatable mouthpiece. The electronic cigarette comprises a battery assembly 1 and an atomizing assembly 2, and the battery assembly 1 and the atomizing assembly 2 connects with each other. The battery assembly 1 comprises a casing 11 and a battery 12 accommodated in the casing 11. The atomizing assembly 2 comprises a mouthpiece 21 and an outer sleeve 22, and the mouthpiece 21 is positioned at the upper portion of the outer sleeve 22. The upper portion of the casing 11 of the battery assembly 1 comprises a side ridge 111. The outer sleeve 22 is hinged to the side ridges 111 through a cardinal axis 3, and the axis of the cardinal axis 3 is vertical to the axis of the casing 11. In a modified embodiment, a total number of the side ridges 111 is two, so that it could fix the atomizing assembly 2 tightly. The side ridges 111 also have a guide rail groove 112. The cardinal axis 3 is accommodated in the guide rail groove 112, and the cardinal axis 3 is slidable along the guide rail groove 112. The sliding direction of the cardinal axis 3 is the same as the axial direction of the casing 11.

Figure 3:
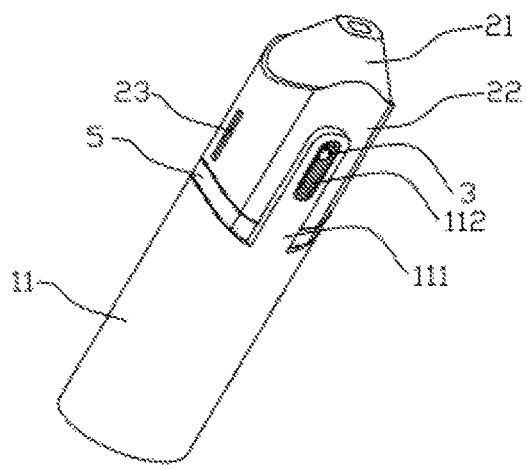
FIG. 3 is a prospective view of the electronic cigarette with a rotatable mouthpiece in using status.
Figure 4:
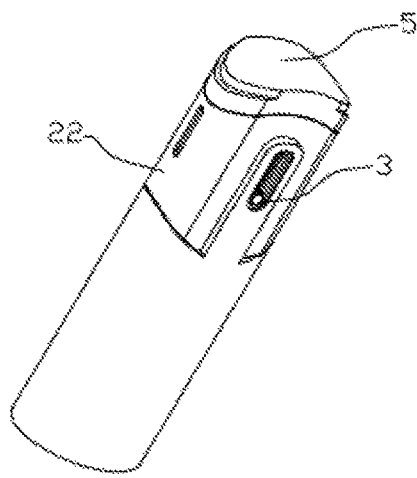
FIG. 4 is a prospective view of the electronic cigarette with a rotatable mouthpiece in accommodation status.
Figure 5:
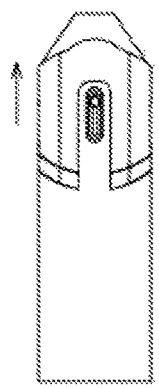
FIG. 5 is a side view of the electronic cigarette with a rotatable mouthpiece in using status.
Figure 6:
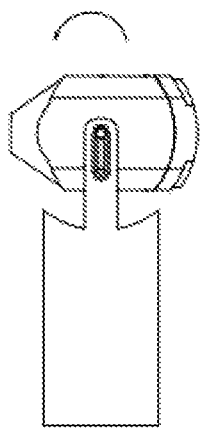
FIG. 6 is a side view of the electronic cigarette with a rotatable mouthpiece in a first intermediate status.
Figure 7:
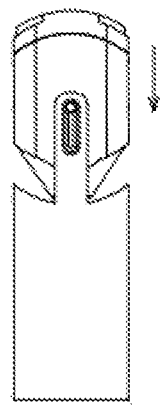
FIG. 7 is a side view of the electronic cigarette with a rotatable mouthpiece in a second intermediate status.
Figure 8:
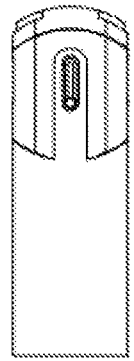
FIG. 8 is a side view of the electronic cigarette with a rotatable mouthpiece in accommodation status.

The upper portion of the casing 11 of the battery assembly 1 comprises a groove 14. In using status, referring to FIGS. 1, 3 and 5, the cardinal axis 3 is formed in the upper portion of the guide rail groove 112, and the end portion of the outer sleeve 22 is accommodated in groove 14. After using, in the process of accommodation, referring to FIG. 5, the whole atomizing assembly 2 is firstly drawn along a direction of the guide rail groove, so that the end portion of the atomizing assembly 2 separates from groove 14, and then the atomizing assembly 2 could be rotated. After that, referring to FIG. 6, the whole atomizing assembly 2 is rotated 180 degrees. Following that, referring to FIG. 7, the atomizing assembly 2 is pushed in a direction toward the battery assembly, so that the atomizing assembly 2 can move downwards along the direction of the guide rail groove 112, until the cardinal axis 3 is positioned at the bottom of the guide rail groove 112. And then, the mouthpiece 21 is accommodated in groove 14. Referring to FIG. 3 in using status and FIG. 4 in total accommodation status, in both statuses the outer surface of outer sleeve 22 laminates with the upper portion of the casing 11 tightly, so that to avoid the entrance of water and dust. In the present disclosure, the mouthpiece 21 is rotatable accommodated easily and quickly with no extra device used. At the same time, time and space are saved for user and the user privacy is also protected. When the electronic cigarette changes from accommodation status to using status, the steps of operating the atomizing assembly 2 are a reverse process of the above described steps, and we will not repeat here.

In the first embodiment of the present disclosure, the atomizing assembly 2 also has a cartridge 4, and the cartridge 4 is filled with tobacco liquid, tobacco cream, solid tobacco materials or other smoking substance. The cartridge 4 and outer sleeve 22 are fixed as a one-piece structure. The mouthpiece 21 and outer sleeve 22 are a one-piece structure. The outer sleeve 22 also has an end cap 5, and the end cap 5 and the mouthpiece 21 are placed at two opposite ends of the outer sleeve 22 respectively. The outer sleeve 22 also has a window 23. The window 23 is configured in a vertical direction, so that users could check the left quantity of smoking substance easily.

Figure 9:
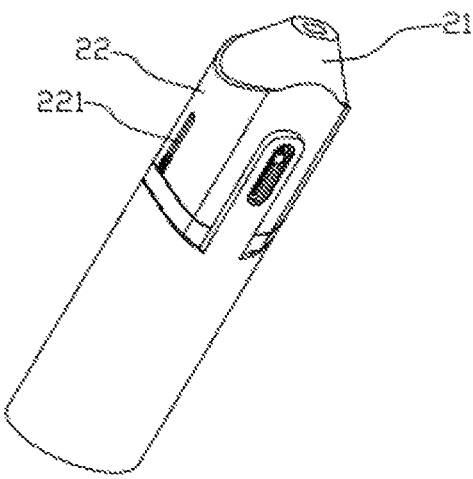
FIG. 9 is a prospective view of the second embodiment of the electronic cigarette with a rotatable mouthpiece in using status.
Figure 10:
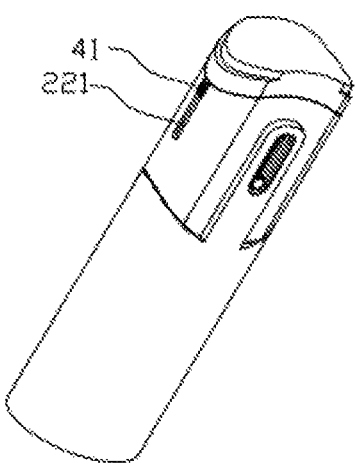
FIG. 10 is a prospective view of the second embodiment of the electronic cigarette with a rotatable mouthpiece in accommodation status.
Figure 11:
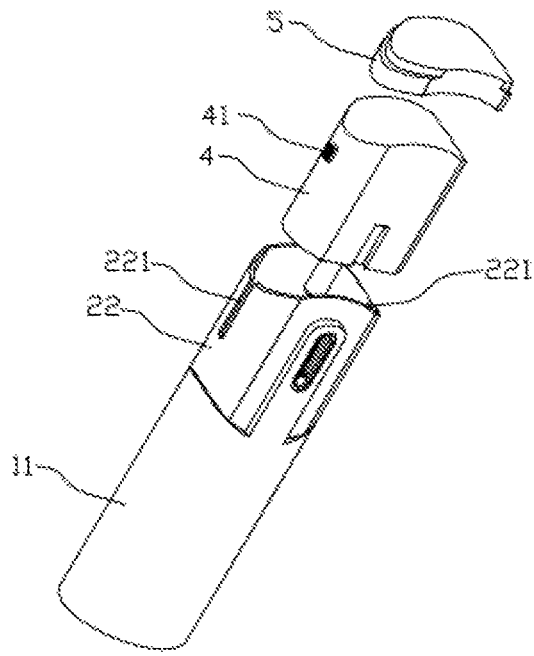
FIG. 11 is an exploded view of the second embodiment of the electronic cigarette with a rotatable mouthpiece in accommodation status.

In a second embodiment of the present disclosure, referring to FIGS. 9-11, the main structure of the embodiment is the same as the structure of the first embodiment. The difference is that the cartridge 4 and outer sleeve 22 are a detachable structure. The object of the difference is that, user can renew a new cartridge 4 when the smoking substance in the old one is exhausted, and at the same time the outer sleeve 22 and the mouthpiece 21 could be used continually, so to save the consumption of material. In the second embodiment, the outer sleeve 22 has vertical slots 221 defined in a side surface, and the cartridge 4 has protruding portions 41 formed on the outer surface. The position of the protruding portions 41 is correspondent with the position of the slots 221. The protruding portion 41 protrudes from the outer surface of the outer sleeve 22. When the cartridge 4 is installed in outer sleeve 22, the protruding portion 41 slides along the slots 221, so that it can be installed successfully. The cartridge 4 is fixedly positioned in the outer sleeve 22, and could not be twisted. After the installation of the cartridge 4, close the end cap 5. Then rotate the whole atomizing assembly 2, so that the mouthpiece 21 is in the upper position. The electronic cigarette is in the status of ready to be used.

In the second embodiment of the present disclosure, in a modified embodiment, a total number of the slots 221 is two, and a total number of the protruding portion 41 is two, correspondently. That is, the slots 221 are configured to position at two side edges of the outer sleeve 22 symmetrically. The benefit is, only two fingers are needed to clamp the protruding portion 41 to remove the cartridge 4 when installing or detaching the cartridge 4. Another object of the slots 221 is that, users could check the consumption of the smoking substance in the cartridge 4 through slots 221, so that users can replace a new cartridge 4 before exhausted to avoid dry heating.

Figure 12:
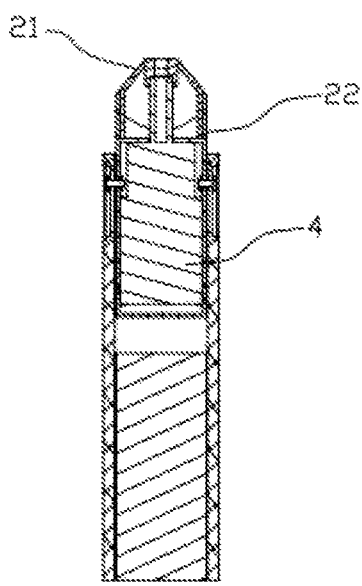
FIG. 12 is a cross-section of the third embodiment of the electronic cigarette with a rotatable mouthpiece in using status.
Figure 13:
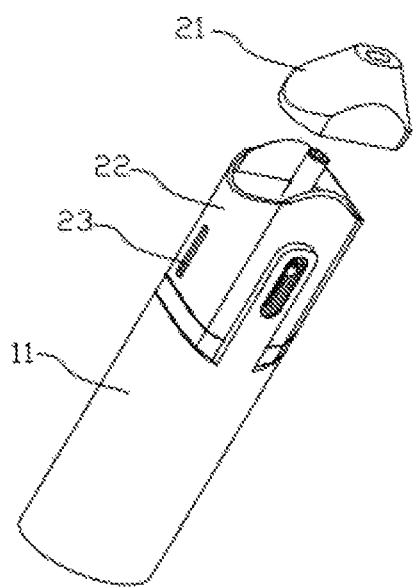
FIG. 13 is an exploded view of the third embodiment of electronic cigarette with a rotatable mouthpiece in using status.

In a third embodiment of the present disclosure, referring to FIGS. 12-13, the main structure of the embodiment is the same as the structure of the first embodiment. The difference is that, the mouthpiece 21 and the outer sleeve 22 are a detachable structure, and the end portion of the mouthpiece 21 is accommodated in a groove of the upper portion of the outer sleeve 22. The object is that, users could replace mouthpieces with mouthpieces of different shapes according to personal interest. Another object of the disclosure is, when the mouthpiece is aging or destroyed, user can replace the mouthpiece and the outer sleeve 22 could be used continually, so that users could save cost and give the users more options.

In a fourth embodiment of the present disclosure, the main structure of the embodiment is the same as the structure of the first embodiment. The difference is that, the cartridge 4 and the outer sleeve 22 are a detachable structure, and at the same time the mouthpiece 21 and the outer sleeve 22 are also a detachable structure.

In a fifth embodiment of the present disclosure, the main structure of the embodiment is the same as the structure of the first embodiment. The difference is that, a guide rail groove is defined in the outer sleeve of the atomizing assembly, and the cardinal axis is formed on the casing of the battery assembly. The cardinal axis is slidable along the guide rail groove, and the sliding direction of the cardinal axis is the same as the axial direction of the casing. When draw the whole atomizing assembly along the direction of the guide rail groove, the end portion of the atomizing assembly is separated from groove, and the whole atomizing assembly could be rotated 0-180 degrees along cardinal axis.

The above description is given by way of example, and not limitation. Given the above disclosure, one skilled in the art could devise variations that are within the scope and spirit of the disclosure disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An electronic cigarette with a rotatable mouthpiece, comprising:
    a battery assembly, the battery assembly comprising a battery and a casing;
    an atomizing assembly, connected with the battery assembly;
    wherein the atomizing assembly comprises:
    a mouthpiece;
    a cartridge; and
    an outer sleeve, the outer sleeve being hinged to the casing through a pin;
    wherein the pin is accommodated in a guide rail groove;
    the pin is slidable along the guide rail groove; and
    a sliding direction of the pin is the same as an axial direction of the casing;
    wherein in accommodation status, the pin is positioned at bottom of the guide rail groove, and the mouthpiece is accommodated in a groove of an upper portion of the casing;
    wherein in using status, the pin is positioned at an upper or middle portion of the guide rail groove.

2. The electronic cigarette according to claim 1, wherein:
    an upper side of the casing of the battery assembly comprises a side ridge;
    the outer sleeve is hinged to the side ridge through the pin; and
    the guide rail groove is defined in the side ridge.

3. The electronic cigarette according to claim 1, wherein:
    in using status, an end portion of the outer sleeve is accommodated in a groove of the upper portion of the casing.

4. The electronic cigarette according to claim 1, wherein:
    an outer surface of the outer sleeve is fit with an upper portion of the casing totally.

5. The electronic cigarette according to claim 4, wherein in the accommodation status, the outer sleeve abuts against the upper portion of the casing.

6. The electronic cigarette according to claim 1, wherein:
    the mouthpiece of the atomizing assembly and the outer sleeve are a one-piece structure or a detachable structure.

7. The electronic cigarette according to claim 1, wherein: the cartridge and outer sleeve are a detachable structure.

8. The electronic cigarette according to claim 7, wherein:
    the outer sleeve has vertical slots defined in a side surface;
    the cartridge has a protruding portion formed on an outer surface;
    the position of the protruding portions is correspondent with the position of the slots; and
    the protruding portions protrude from the outer surface of the outer sleeve.

9. The electronic cigarette according to claim 8, wherein:
    a total number of the slots is two; and
    a total number of the protruding portions is two, correspondingly.

10. The electronic cigarette according to claim 1, wherein:
    the outer sleeve has an end cap, and the end cap and the mouthpiece are placed on two sides of the outer sleeve respectively.

* * * * *